(12) United States Patent
Kikta et al.

(10) Patent No.: US 8,673,330 B2
(45) Date of Patent: Mar. 18, 2014

(54) INSECTICIDAL COMPOSITIONS SUITABLE FOR USE IN PREPARATION OF INSECTICIDAL GRANULAR FERTILIZER AND INSECTICIDAL FORMULATIONS

(75) Inventors: Edward Kikta, Langhorne, PA (US); Larry G. Faehl, Chambersburg, PA (US); Kim Watson, Indian Harbour Beach, FL (US); David R. Kilanowski, Dublin, OH (US); Robert Radabaugh, Marysville, OH (US); Coby L. Crane, Howell, NJ (US)

(73) Assignees: FMC Corporation, Philadelphia, PA (US); The Scotts Company LLC, Marysville, OH (US)

( * ) Notice: Subject to any disclaimer, the term of this patent is extended or adjusted under 35 U.S.C. 154(b) by 0 days.

(21) Appl. No.: 13/545,288

(22) Filed: Jul. 10, 2012

(65) Prior Publication Data

US 2012/0277103 A1    Nov. 1, 2012

Related U.S. Application Data

(62) Division of application No. 11/718,557, filed as application No. PCT/US2005/040262 on Nov. 7, 2005, now Pat. No. 8,247,446.

(60) Provisional application No. 60/625,918, filed on Nov. 8, 2004.

(51) Int. Cl.
*A01N 25/32* (2006.01)
*A01N 25/00* (2006.01)

(52) U.S. Cl.
USPC .......... 424/409; 71/64.13; 424/405; 424/417; 514/341; 514/531; 514/738

(58) Field of Classification Search
None
See application file for complete search history.

(56) References Cited

U.S. PATENT DOCUMENTS

| 5,783,203 | A | 7/1998 | Schutte et al. |
| 6,468,555 | B1 | 10/2002 | Nakamura |
| 7,531,187 | B2 | 5/2009 | Jadhav et al. |
| 2008/0103048 | A1 | 5/2008 | Radabaugh et al. |
| 2008/0287425 | A1 | 11/2008 | Watson et al. |
| 2008/0319023 | A1 | 12/2008 | Richman et al. |

FOREIGN PATENT DOCUMENTS

| GB | 2230954 | 11/1990 |
| WO | 0245507 | 6/2002 |

OTHER PUBLICATIONS

Martin A. et al. "Pesticides and Formulation Technology", Purdue Extension ppp-31, Purdue University, Jan. 2011.

*Primary Examiner* — Neil Levy
(74) *Attorney, Agent, or Firm* — FMC Corporation

(57) ABSTRACT

Insecticidal compositions suitable for use in preparation of insecticidal granular fertilizer and insecticidal formulations comprising a pyrethroid and a glycol present in a concentration of from 40.0% by weight to 99.0% by weight based upon the total weight of all components in the composition is disclosed.

9 Claims, 1 Drawing Sheet

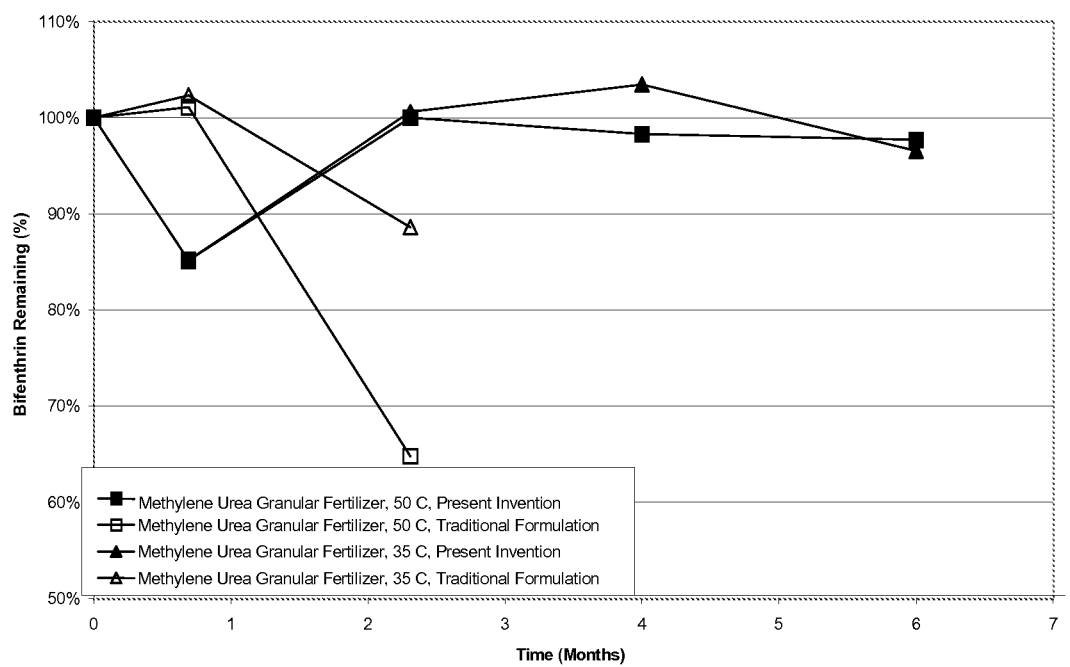

INSECTICIDAL COMPOSITIONS SUITABLE FOR USE IN PREPARATION OF INSECTICIDAL GRANULAR FERTILIZER AND INSECTICIDAL FORMULATIONS

This application claims the benefit of U.S. Provisional Application No. 60/625,918, filed Nov. 8, 2004.

FIELD OF THE INVENTION

The present invention relates to the field of chemical compositions and formulations. In particular, the invention provides an insecticidal composition suitable for use in preparation of insecticidal granular fertilizer and insecticidal formulations.

BACKGROUND OF THE INVENTION

To enable the efficient elimination or control of unwanted insects in combination with providing nutrients for plants to combat adverse environmental conditions (heat, dry weather, physical contact with animals) it is desirable to formulate an effective chemical insecticide (liquid concentrate) for use in preparation of insecticidal granular fertilizer and insecticidal formulations (end use products). Formulations of pesticides combined with fertilizers are desirable in agricultural and related endeavors due to the multiple benefits conveyed by just one application. One application of such a combination or formulation provides nutrients for the plant growth, while eliminating or controlling unwanted insects that can also affect the health and vitality of the desirable plants.

Formulations containing insecticides and fertilizers have been practiced in the art, but problems with the chemical stability of the insecticides in such formulations have caused efficacy issues. When an insecticide is formulated with a granular fertilizer, the fertilizer may contribute to accelerated chemical degradation of the insecticide. Chemical degradation is an important problem because there may be no physical sign of the degradation and resultant loss of efficacy until used in an actual field application. Since a small change in composition can adversely impact efficacy and ultimately may cause a total loss of efficacy, the chemical stability of the insecticide in such a formulation is of primary importance. The issue of chemical stability of insecticidal compositions for use in preparation of insecticidal granular fertilizer and insecticidal formulations has been addressed with the composition of the present invention.

SUMMARY OF THE INVENTION

The present invention is directed to an insecticidal composition suitable for use in preparation of insecticidal granular fertilizer and insecticidal formulations comprising a pyrethroid and a glycol selected from the group consisting of hexylene glycol, diethylene glycol, triethylene glycol, polyethylene glycol and glycerine, the glycol being present in a concentration of from 40.0% by weight to 99.0% by weight based upon the total weight of all components in the composition.

BRIEF DESCRIPTION OF THE DRAWING

FIG. 1 demonstrates the results of the stability testing and compares the formulation of the present invention with a traditional formulation in the art for bifenthrin in combination with a methylene urea granular fertilizer.

DETAILED DESCRIPTION OF THE INVENTION

As used in this specification and unless otherwise indicated the term "insecticide" refers to a molecule or combination of molecules that repels, retards, or kills insects, and can be used for crop protection, edifice protection, turf protection, or protection of a person.

The modifier "about" is used herein to indicate that certain preferred operating ranges, such as ranges for molar ratios for reactants, material amounts, and temperature, are not fixedly determined. The meaning will often be apparent to one of ordinary skill. For example, a recitation of a temperature range of about 120° C. to about 135° C. in reference to, for example, an organic chemical reaction would be interpreted to include other like temperatures that can be expected to favor a useful reaction rate for the reaction, such as 105° C. or 150° C. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

The term "ambient temperature" as utilized herein shall mean any suitable temperature found in a laboratory or other working environment, and is generally not below about 15° C. nor above about 30° C.

The present invention is directed to an insecticidal composition suitable for use in preparation of insecticidal granular fertilizer and insecticidal formulations comprising a pyrethroid and a glycol selected from the group consisting of hexylene glycol, diethylene glycol, triethylene glycol, polyethylene glycol and glycerine, the glycol being present in a concentration of from 40.0% by weight to 99.0% by weight based upon the total weight of all components in the composition.

The pyrethroid may be selected from the group consisting of bifenthrin, zeta-cypermethrin, beta-cypermethrin, cypermethrin, deltamethrin, permethrin, lambda-cyhalothrin, gamma-cyhalothrin, tralomethrin, cyfluthrin, beta-cyfluthrin, esfenvalerate, fluvalinate and natural pyrethrum. Preferably, the pyrethroid is bifenthrin. The pyrethroid may be present in a concentration of from 1.0% by weight to 20% by weight based upon the total weight of all components in the composition.

The composition may further comprise a surfactant selected from the group consisting of non-ionic surfactants and phosphated surfactants. The surfactant may be selected from the group consisting of ethoxylates and ethylene oxide/propylene oxide (EO/PO) block polymers. The surfactant may be selected from ethoxylates of materials such as, but not limited to, alkyl phenols, alcohols and sorbitans. Preferably, the surfactant is nonyl phenol ethoxylate 9.5 mole. The surfactant may be present in a concentration of from 0.02% by weight to 30.0% by weight based upon the total weight of all components in the composition.

The composition may further comprise an insecticidally effective amount of one or more additional insecticides selected from the group consisting of imidacloprid, flonicamid, nithiazine, thiamethoxam, dinotefuran, nitenpyram, thiacloprid, clothianadin and chlorfenapyr.

Another embodiment of the present invention is a formulation comprising a pyrethroid, a glycol selected from the group consisting of hexylene glycol, diethylene glycol, triethylene glycol, polyethylene glycol and glycerine, the glycol being present in a concentration of from 40.0% by weight to 99.0% by weight based upon the total weight of all components in the formulation and a granular fertilizer. The granular fertilizer may be selected from the group consisting of nitrogen, phosphate and potassium fertilizers. The granular fertilizer may be present in a concentration of from 95.00% by weight to 99.99% by weight based upon the total weight of all components in the formulation. Other granular matrices may be used in place of the granular fertilizer such as, but not limited to, sand, DG Lite and corn cob.

Another embodiment of the present invention is a formulation comprising a pyrethroid, a glycol selected from the group consisting of hexylene glycol, diethylene glycol, triethylene glycol, polyethylene glycol and glycerine, the glycol being present in a concentration of from 40.0% by weight to 99.0% by weight based upon the total weight of all components in the formulation, a surfactant selected from the group consisting of non-ionic surfactants and phosphated surfactants and a granular fertilizer. The granular fertilizer may be selected from the group consisting of nitrogen, phosphate and potassium fertilizers. The granular fertilizer may be present in a concentration of from 95.0% by weight to 99.99% by weight based upon the total weight of all components in the formulation. Other granular matrices may be used in place of the granular fertilizer such as, but not limited to, sand, DG Lite and corn cob.

Yet another embodiment of the present invention is a formulation comprising a pyrethroid, a glycol selected from the group consisting of hexylene glycol, diethylene glycol, triethylene glycol, polyethylene glycol and glycerine, the glycol being present in a concentration of from 40.0% by weight to 99.0% by weight based upon the total weight of all components in the formulation, an insecticidally effective amount of one or more additional insecticides selected from the group consisting of imidacloprid, flonicamid, nithiazine, thiamethoxam, dinotefuran, nitenpyram, thiacloprid, clothianadin and chlorfenapyr and a granular fertilizer. The granular fertilizer may be selected from the group consisting of nitrogen, phosphate and potassium fertilizers. The granular fertilizer may be present in a concentration of from 95.0% by weight to 99.99% by weight based upon the total weight of all components in the formulation. Other granular matrices may be used in place of the granular fertilizer such as, but not limited to, sand, DG Lite and corn cob.

An especially preferred embodiment of the present invention is an insecticidal composition suitable for use in preparation of insecticidal granular fertilizer and insecticidal formulations comprising from 2.0% to 10.0% of bifenthrin and from 90.0% to 98.0% of hexylene glycol, wherein all % are % by weight based upon the total weight of all components in the composition.

Another especially preferred embodiment of the present invention is an insecticidal composition suitable for use in preparation of insecticidal granular fertilizer and insecticidal formulations comprising from 2.0% to 10.0% of bifenthrin, from 60.0% to 98.0% of hexylene glycol, and from 0.02% to 30.0% of an ethoxylate, wherein all % are % by weight based upon the total weight of all components in the composition.

The present invention encompasses a method of controlling unwanted insects and providing nutrients to plants, the method comprising applying to an area infested with such insects and containing such plants an effective amount of the compositions or formulations of this invention.

The present invention also encompasses a process from preparing a composition or formulation of this invention comprising melting a pyrethroid and dissolving the pyrethroid in a glycol and optionally a surfactant. The process may further comprise applying the resultant mixture onto a granular fertilizer.

The present invention, previously described, addresses the problem of chemical degradation of insecticidal compositions when applied to a granular fertilizer. The composition of the present invention has improved chemical stability when used to prepare an insecticidal granular fertilizer.

The compositions of the present invention are further illustrated by the examples below. The examples serve only to illustrate the invention and should not be interpreted as limiting since further modifications of the disclosed invention will be apparent to those skilled in the art. All such modifications are deemed to be within the scope of the invention as defined in the claims.

Example 1

This example illustrates one protocol for the preparation of a composition (Composition A) of the present invention.

An amount of 0.9 grams of bifenthrin was melted and kept warm in liquid form. In a separate container, a mixture of 3.14 grams of nonyl phenol ethoxylate 9.5 mole and 5.96 grams of hexylene glycol was combined and agitated. To this mixture was added the 0.9 grams of bifenthrin. The resultant mixture was agitated until the bifenthrin was dispersed and well mixed to produce a composition of the present invention.

Example 2

This example illustrates one protocol for the preparation of a composition (Composition B) of the present invention.

An amount of 1.37 grams of bifenthrin was warmed and melted into liquid form. To the bifenthrin was added 8.63 grams of hexylene glycol. The resultant mixture was agitated until the bifenthrin was dispersed and well mixed to produce a composition of the present invention.

Example 3

This example illustrates one protocol for the preparation of a composition (Composition C) of the present invention.

An amount of 2.0 grams of bifenthrin was warmed and melted into liquid form. To the bifenthrin was added 8.0 grams of hexylene glycol. The resultant mixture was agitated until the bifenthrin was dispersed and well mixed to produce a formulation of the present invention.

Example 4

This example illustrates one protocol for the preparation of a composition (Composition D) of the present invention.

An amount of 0.913 grams of bifenthrin was melted and kept warm in liquid form. In a separate container, a mixture of 2.98 grams of phosphate ester surfactant (available from Chemron in Paco Robles, Calif.)) and 6.107 grams of hexylene glycol was combined and agitated. To this mixture was added the 0.913 grams of bifenthrin. The resultant mixture was agitated until the bifenthrin was dispersed and well mixed to produce a composition of the present invention.

Example 5

This example illustrates one protocol for the preparation of a composition (Composition E) of the present invention.

An amount of 0.947 grams of bifenthrin was melted and kept warm in liquid form. In a separate container, a mixture of 3.14 grams of nonyl phenol ethoxylate 9.5 mole and 5.913 grams of hexylene glycol was combined and agitated. To this mixture was added the 0.947 grams of bifenthrin. The resultant mixture was agitated until the bifenthrin was dispersed and well mixed to produce a composition of the present invention.

Example 6

This example illustrates one protocol for the preparation of a composition (Composition F) of the present invention.

An amount of 1.37 grams of bifenthrin was warmed and melted into liquid form. To the bifenthrin was added 8.63 grams of hexylene glycol. The resultant mixture was agitated until the bifenthrin was dispersed and well mixed to produce a composition of the present invention.

Example 7

This example illustrates one protocol for the possible preparation of a formulation (Formulation A) of the present invention.

An amount 1.17 grams of the formulation prepared in example 1 can be sprayed onto 155.0 grams of a methylene urea granular fertilizer (available from Scotts in Marysville, Ohio) in a ribbon type mixer to produce a formulation of the present invention.

Example 8

This example illustrates one protocol for the possible preparation of a formulation (Formulation B) of the present invention.

An amount 1.17 grams of the formulation prepared in example 2 can be sprayed onto 155.0 grams of a methylene urea granular fertilizer (available from Scotts in Marysville, Ohio) in a ribbon type mixer to produce a formulation of the present invention.

Example 9

This example illustrates one protocol for the possible preparation of a formulation (Formulation C) of the present invention.

An amount 1.17 grams of the formulation prepared in example 3 can be sprayed onto 155.0 grams of a methylene urea granular fertilizer (available from Scotts in Marysville, Ohio) in a ribbon type mixer to produce a formulation of the present invention.

Example 10

This example illustrates one protocol for the preparation of a formulation (Formulation D) of the present invention.

An amount 1.17 grams of the formulation prepared in example 4 was sprayed onto 155.0 grams of a methylene urea granular fertilizer (available from Scotts in Marysville, Ohio) in a ribbon type mixer to produce a formulation of the present invention.

Example 11

This example illustrates one protocol for the possible preparation of a formulation (Formulation E) of the present invention.

An amount 1.17 grams of the formulation prepared in example 5 can be sprayed onto 155.0 grams of a methylene urea granular fertilizer (available from Scotts in Marysville, Ohio) in a ribbon type mixer to produce a formulation of the present invention.

Example 12

This example illustrates one protocol for the possible preparation of a formulation (Formulation F) of the present invention.

An amount 1.17 grams of the formulation prepared in example 6 can be sprayed onto 155.0 grams of a methylene urea granular fertilizer (available from Scotts in Marysville, Ohio) in a ribbon type mixer to produce a formulation of the present invention.

Example 13

Comparative Stability Studies

This example sets forth stability studies that were performed on formulations prepared in accordance with the present invention.

The pyrethroid stability of a formulation of the present invention was screened in an accelerated stability test by formulating bifenthrin (a pyrethroid), a glycol and a surfactant with a methylene urea granular fertilizer and storing it at 35 C and 50 C for 6 months. The present invention's stability was compared with that of a traditional formulation in the art. Formulation D of Example 10 represented the present invention in this study. The traditional formulation contained bifenthrin, glyceryl triacetate, hydrotreated light petroleum distillate and bis(-methylethyl)-1,1'-biphenyl combined with Scotts methylene urea granular fertilizer. Note that stability test of storage at 50 C for ten weeks has previously been found to be indicative of 2 years of on-shelf active ingredient stability from chemical degradation.

FIG. 1 demonstrates the results of the stability testing and compares the formulation of the present invention with a traditional formulation in the art for bifenthrin in combination with a methylene urea granular fertilizer.

While this invention has been described with an emphasis upon preferred embodiments, it will be obvious to those of ordinary skill in the art that variations in the preferred compositions and methods may be used and that it is intended that the invention may be practiced otherwise than as specifically described herein. Accordingly, this invention includes all modifications encompassed within the spirit and scope of the invention as defined by the claims that follow.

What is claimed is:

1. A fertilizer formulation comprising a) bifenthrin;

b) a glycol selected from the group consisting of hexylene glycol, diethylene glycol, triethylene glycol, polyethylene glycol and glycerine present in a concentration of from 40.0% by weight to 99.0% by weight based upon the total weight of bifenthrin plus glycol; and c) a granular fertilizer;

wherein the formulation is in granular form.

2. The formulation of claim 1, wherein the granular fertilizer is selected from the group consisting of nitrogen, phosphate and potassium fertilizers.

3. The formulation of claim 1, wherein the granular fertilizer is present in a concentration of from 95.0% by weight to 99.99% by weight based upon the total weight of all components in the formulation.

4. A fertilizer formulation comprising a) bifenthrin;

b) a glycol selected from the group consisting of hexylene glycol, diethylene glycol, triethylene glycol, polyethylene glycol and glycerine present in a concentration of from 40.0% by weight to 99.0% by weight based upon the total weight of bifenthrin plus glycol;

c) a surfactant selected from the group consisting of nonionic surfactants and phosphated surfactants; and d) a granular fertilizer;

wherein the formulation is in granular form.

5. The formulation of claim 4, wherein the granular fertilizer is selected from the group consisting of nitrogen, phosphate and potassium fertilizers.

6. The formulation of claim 4, wherein the granular fertilizer is present in a concentration of from 95.0% by weight to 99.99% by weight based upon the total weight of all components in the composition.

7. A fertilizer formulation comprising a) a bifenthrin;

b) a glycol selected from the group consisting of hexylene glycol, diethylene glycol, triethylene glycol, polyethylene glycol and glycerine present in a concentration of from 40.0% by weight to 99.0% by weight based upon the total weight of bifenthrin plus glycol;

c) an insecticidally effective amount of imidacloprid; and d) a granular fertilizer;

wherein the formulation is in granular form.

8. The formulation of claim 7, wherein the granular fertilizer is selected from the group consisting of nitrogen, phosphate and potassium fertilizers.

9. The formulation of claim 7, wherein the granular fertilizer is present in a concentration of from 95.0% by weight to 99.99% by weight based upon the total weight of all components in the composition.

\* \* \* \* \*